(12) United States Patent
Piercey et al.

(10) Patent No.: US 11,434,211 B2
(45) Date of Patent: Sep. 6, 2022

(54) SYNTHESIS OF 5-NITROTETRAZOLE

(71) Applicant: Purdue Research Foundation, West Lafayette, IN (US)

(72) Inventors: Davin Glenn Piercey, Lafayette, IN (US); Timothy D. Manship, Zionsville, IN (US); Dawson Michael Smith, Marana, AZ (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

(21) Appl. No.: 17/221,863

(22) Filed: Apr. 5, 2021

(65) Prior Publication Data

US 2022/0135530 A1    May 5, 2022

Related U.S. Application Data

(60) Provisional application No. 63/039,492, filed on Jun. 16, 2020.

(51) Int. Cl.
    *C07D 257/06*      (2006.01)
(52) U.S. Cl.
    CPC ................... *C07D 257/06* (2013.01)

(58) Field of Classification Search
    CPC .................................................... C07D 257/06
    See application file for complete search history.

(56) References Cited

PUBLICATIONS

Zorn, et al. J. Phys. Chem. B 2006, 110, pp. 11110-11119.*

* cited by examiner

*Primary Examiner* — Shawquia Jackson
(74) *Attorney, Agent, or Firm* — Purdue Research Foundation

(57) ABSTRACT

This disclosure shows the ability of a readily-available oxidizer to achieve oxidation of 5-amino-1H-tetrazole (5-AT) to 5-nitrotetrazole (5-NT) in high yields in a single pot synthesis. This strategy reduces the synthesis of this important energetic material down to a single step and eliminates highly sensitive diazonium and copper salt primary explosive intermediates. The overall yield of this process is 48-53% and the resultant aqueous solution of product effectively used for the preparation of nitrotetrazole-containing primary explosive DBX-1. Unlike current methods of nitrotetrazole preparation, the novel method is entirely solution-based and prepares a final solution of sodium nitrotetrazolate, never once needing to handle energetic intermediates or products, making it a much safer method of nitrotetrazole preparation.

12 Claims, 2 Drawing Sheets

SYNTHESIS OF 5-NITROTETRAZOLE

CROSS-REFERENCE TO RELATED APPLICATION

This application claims the priority benefit of U.S. Provisional Patent application No. 63/039,492, filed Jun. 16, 2020, which is incorporated herein by reference in its entirety.

GOVERNMENT RIGHTS

This invention was made with government support under Award No. N00014-19-1-2089 awarded by the Office of Naval Research. The government has certain rights in the invention.

TECHNICAL FIELD

The present disclosure relates to a novel synthesis of 5-nitrotetrazole via the direct oxidation of 5-aminotetrazole in a single-pot synthesis.

BACKGROUND

This section introduces aspects that may help facilitate a better understanding of the disclosure. Accordingly, these statements are to be read in this light and are not to be understood as admissions about what is or is not prior art.

Primary explosives are energetic materials in which prompt detonation occurs with appropriate thermal, physical, or electrical stimulus. The detonation from the primary explosive transitions to the secondary explosive main charge. Primary explosives, such as lead azide and lead styphnate have had widespread use, however the harmful effects of lead have resulted in a significant push towards "green" primaries free of toxic heavy metals.

5-nitrotetrazole and particularly its sodium salt, sodium 5-nitrotetrazole (NaNT.2H$_2$O) is a valuable precursor to the next generation of "green" energetics. Though NaNT in its anhydrous state suffers from hygroscopicity and extreme sensitivity making it unviable as an energetic material on its own, it has served as a precursor for the synthesis of notable lead-free primaries; the arguably most important of which is Copper (I) 5-nitrotetrazolate (DBX-1) which serves as a primary replacing lead azide in percussion caps and stab detonators. Other important next-generation primary explosives employing NaNT as a precursor are silver nitrotetrazolate and bis-(5-nitro-2H tetrazolato-N2)tetraamino cobalt (III) perchlorate (BNCP).

There are currently two primary methods employed to make NaNT. The first method was discovered by von Herz in the 1930s [See U.S. Pat. No. 2,066,954] and is based on the Sandmeyer reaction with 5-aminotetrazole (5-AT) as the precursor. This approach suffered from microdetonations related to the 5-diazotetrazolate intermediate and a required filtration of the sensitive acidic intermediate hydronium Copper(II)-tris(5-nitrotetrazolate) Trihydrate (generally abbreviated to Cu(NT)$_2$.HNT). Klapötke et. al [See T. M. Klapotke, et al. *Anorg. Allg. Chem.*, 2013, 639(5), p. 681] were able to avoid isolation of the sensitive Cu(NT)$_2$.HNT intermediate by treating the reaction directly with a strong base and reducing the occurrence of microdetonations by maintaining a low temperature and slow addition rate of the 5-AT solution. Furthermore, they were able to identify impurities such as 1H-tetrazole, 5-aminotetrazole, and 5,5'-bitetrazole, which were thought to negatively impact the formation of DBX-1 when the produced sodium nitrotetrazolate was used for that purpose. The other known method of synthesis was discovered by Koldobskii and Ostrovskii et al. [See G. I. Koldobskii, et al., J. Org. Chem., 1997, 33(12), p. 1771], which was a non-catalytic Sandmeyer reaction. This avoided the use of sacrificial copper sulfate "catalyst" and was able to achieve 70-80% yield by running the Sandmeyer reaction at elevated temperatures (50-100° C.). Microdetonations were still prevalent and a suggested method to avoid microdetonations was to feed a solution of 5-AT in sulfuric acid under an aqueous layer of sodium nitrite well away from the reaction vessel walls, but this led to sodium nitrite and other impurities in the product, making it unsuitable for synthesis of some primary explosives [See A. Y. Zhilin, M. A. Ilyushin, *Russ. J. Appl. Chem.*, 2001, 74(1), p. 99]. However, overall there is no literature precedent for the oxidation of the amine of 5-aminotetrazole amine to a nitro group.

Therefore, there is an unmet need for a novel synthesis of 5-nitrotetrazole via simpler and more straightforward method.

SUMMARY

The present disclosure relates to a novel synthesis of 5-nitrotetrazole via the direct oxidation of 5-aminotetrazole in a single-pot synthesis.

In one embodiment, the present disclosure provides a method of preparing a compound of Formula I:

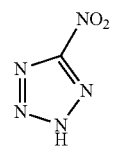

I or any salt thereof,
wherein the method comprises:
providing a solvent system comprising a polar aprotic organic solvent and/or water;
providing 5-amino-1H-tetrazole or any salt thereof;
providing a superoxide anion source (O$_2^-$);
providing a crown ether and/or a molecular sieves;
adding said 5-amino-1H-tetrazole or any salt thereof, said superoxide anion source, said crown ether and/or a molecular sieves to said solvent system; and
allowing said 5-amino-1H-tetrazole or any salt thereof to be oxidized to the compound of Formula I or any salt thereof.

DETAILED DESCRIPTION

Figure 1:
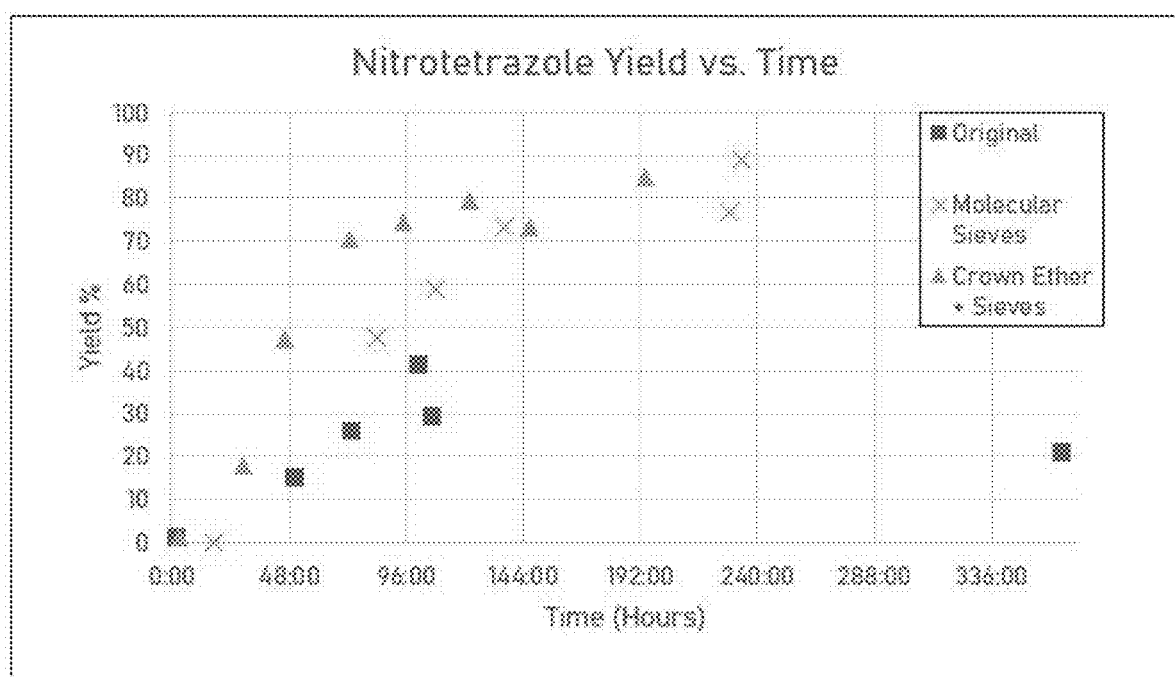
FIG. 1 illustrates In-situ nitrotetrazole yield versus time for modifications in a DMSO solvent.

For the purposes of promoting an understanding of the principles of the present disclosure, reference will now be made to embodiments illustrated in drawings, and specific language will be used to describe the same. It will nevertheless be understood that no limitation of the scope of this disclosure is thereby intended.

The term "crown ether" used in this disclosure refers to cyclic chemical compounds that consist of a ring containing several ether groups. The most common crown ethers are cyclic oligomers of ethylene oxide, the repeating unit being ethyleneoxy, i.e., —CH2CH2O—. Important members of this series are the tetramer (n=4), the pentamer (n=5), and the hexamer (n=6). Any appropriate crown ether may be used. It is not limited to any specific crown ether such as 18-crown-6 as used in the actual synthetic method of the present disclosure.

The term "molecular sieves" refers to any microporous media capable of separating molecules on the basis of size. It can relate to certain carbons and silicas, as well as porous gels/resins for polymer separations, but molecular sieving is best illustrated by the aluminosilicate zeolites. For the purpose of the present disclosure, any appropriate molecular sieves may be used.

In one embodiment, the present disclosure provides a method of preparing a compound of Formula I:

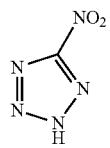

I or any salt thereof,
wherein the method comprises:
providing a solvent system comprising a polar aprotic organic solvent and/or water; providing 5-amino-1H-tetrazole or any salt thereof;
providing a superoxide anion source ($O_2^-$);
providing a crown ether and/or a molecular sieves;
adding said 5-amino-1H-tetrazole or any salt thereof, said superoxide anion source, said crown ether and/or a molecular sieves to said solvent system; and
allowing said 5-amino-1H-tetrazole or any salt thereof to be oxidized to the compound of Formula I or any salt thereof.

In one embodiment regarding the method of preparing a compound of Formula I or any salt thereof, wherein said superoxide anion source ($O_2^-$) may be but is not limited to a superoxide salt of a metal, wherein the metal is an alkali metal, an alkaline earth metal, or a transition metal. In one aspect, the superoxide salt may be a salt of Potassium, Titanium, Tungsten, Vanadium, Zirconium, or Tungsten. In one aspect, the method may use a catalytic amount of superoxide salt and hydrogen peroxide to generate the superoxide anion source. In one aspect, the superoxide salt is a superoxide salt or complex of titanium, tungsten, vanadium, zirconium, ort tungsten.

In one embodiment regarding the method of preparing a compound of Formula I or any salt thereof, wherein said crown ether may be but is not limited to 18-crown-6.

In one embodiment regarding the method of preparing a compound of Formula I or any salt thereof, wherein said polar aprotic organic solvent may be but is not limited to dimethyl sulfoxide (DMSO), dimethylforamide (DMF), acetonitrile (MeCN), sulfolane, or N-Methyl-2-pyrrolidone (NMP).

In one embodiment regarding the method of preparing a compound of Formula I or any salt thereof, wherein said 5-amino-1H-tetrazole or any salt thereof is oxidized at room temperature.

In one embodiment regarding the method of preparing a compound of Formula I or any salt thereof, wherein the compound of Formula I or any salt thereof is prepared under a substantially anhydrous condition prior to any workup step.

In one embodiment regarding the method of preparing a compound of Formula I or any salt thereof, wherein an organic ammonium salt of said compound of Formula I is prepared during one or more workup steps as an intermediate salt of the compound of Formula I, the intermediate salt of the compound of Formula I can be transferred from an aqueous solution to an organic solution by extraction.

In one embodiment regarding the method of preparing a compound of Formula I or any salt thereof, wherein the compound of Formula I is obtained as an alkali metal salt after one or more workup steps.

In one embodiment regarding the method of preparing a compound of Formula I or any salt thereof, wherein the compound of Formula I is obtained as a sodium salt after one or more workup steps.

In one embodiment regarding the method of preparing a compound of Formula I or any salt thereof, wherein the sodium salt of the compound of Formula I is obtained from said organic ammonium salt of said compound of Formula I, by first dissolving said organic ammonium salt in water and then contacting the formed dissolved solution with a sodium-loaded ion exchange resin to give provide an aqueous solution of the sodium salt of the compound of Formula I.

In one embodiment regarding the method of preparing a compound of Formula I or any salt thereof, wherein the organic ammonium salt is a tributylammonium salt.

This disclosure provides a novel preparation of nitrotetrazole via the direct oxidation of 5-aminotetrazole using potassium superoxide. This synthetic route for the preparation of sodium nitrotetrazolate offers increased safety over the current Sandmeyer diazotization synthetic route as it avoids all intermediate sensitive compounds. Furthermore, this method of preparation handles all energetic materials in solution, allowing for a marked safety increase over current methods relying on isolation of intermediate primary explosives.

The method to prepare 5-nitrotetrazole via direct oxidation of anhydrous 5-aminotetrazole as disclosed in this disclosure began with a screen of various polar aprotic solvents including dimethylsulfoxide (DMSO), dimethylformamide (DMF), sulfolane, tetrahydrofuran, and acetonitrile. Initially the only solvents which gave detectable 5-nitrotetrazole after 24 hours of stirring at ambient conditions were DMSO, DMF and sulfolane. Via a quantitative HPLC method, DMSO was found to give the highest yields and was used in all further optimizations (Scheme 1). The quantitative HPLC method was calibrated based on standard solutions prepared from thrice-recrystallized sodium nitrotetrazolate dihydrate as prepared by the literature means.

Scheme 1. Direct oxidation of 5-amino-1H-tetrazole (5-AT,1) to 5-nitro-1H-tetrazole (5-NT, 2)

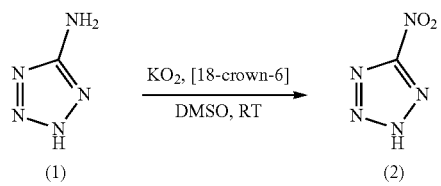

In-situ quantification of these reactions had the inherent difficulty in representative sampling given that the superoxide did not entirely dissolve in the reaction mixture and the mixture was slurry-like. As such, yields mentioned prior to work up should only be taken as rough estimates. By tracking the reaction of 5-aminotetrazole with potassium superoxide in anhydrous DMSO, it was found that after 4.5 days it reached a maximum yield of ~35% which was found to decrease with additional reaction time. (FIG. 1).

It is known that the byproduct of superoxide oxidations of amines is water. Potassium superoxide, in the presence of water, degrades into potassium hydroxide, and strong nucleophiles such as hydroxide are effective at destroying nitro compounds and so addition of molecular sieves was incorporated to sequester the formed water. A further iteration incorporated 18-crown-6 to increase solubility of $KO_2$ in organic solvents. It is shown in FIG. 1 that the incorporation of these modifications to the reaction led to both higher overall yields (~85%) when compared to the reaction without molecular sieves, and, in the case of the crown ether reaction, led to faster completion of the reaction when compared to without crown ether.

Upon reaction completion, the reaction was quenched in excess cold water buffered with ammonium bicarbonate and then filtered to remove solids (residual molecular sieves). To the filtrate, 1 equivalent (relative to starting 5-aminotetrazole) of tributylammonium sodium sulfate was added. The solution was adjusted to pH 6 and the tributylammonium salt of 5-nitrotetrazole was extracted into ethyl acetate. After evaporation of the ethyl acetate solution and ion exchange using a sodium-loaded Amberlyst 15® ion exchange resin, an aqueous solution of sodium 5-nitrotetrazolate was obtained. HPLC Quantification of this solution showed a 48%-53% yield of product.

Figure 2:
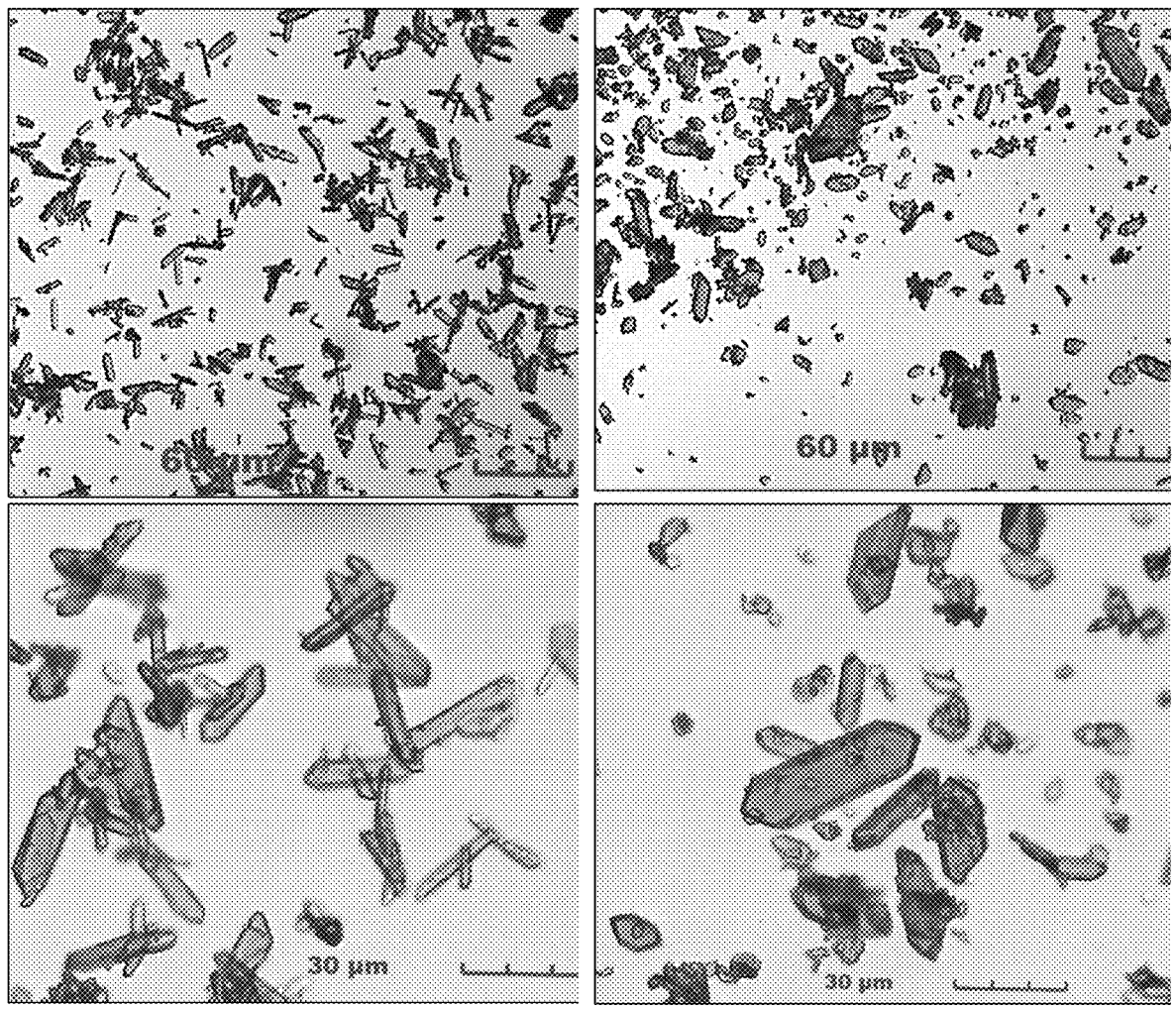
FIG. 2 illustrates DBX-1 Crystals synthesized from literature sodium nitrotetrazolate (left) and from NaNT prepared by the method of the present disclosure.

Impurities in sodium nitrotetrazolate solutions are known to cause issues in the synthesis of DBX-1 [See T. M. Klapötke, *Anorg. Allg. Chem.*, 2013, 639(5), p. 681]. The ultimate test of the utility of our new route to sodium nitrotetrazolate is its ability to function in the synthesis of DBX-1 without further purification. We prepared DBX-1 from copper (I) chloride and our NaNT solution as well as a solution of purified literature-prepared NaNT. The sodium nitrotetrazolate prepared by our method successfully formed DBX-1. Microscopy images of the DBX-1 prepared from our sodium nitrotetrazolate vs. literature are shown in FIG. 2.

The DBX-1 generated from our sodium nitrotetrazolate is overall similar in morphology and particle sizes to that prepared from literature sodium nitrotetrazolate, however they are distinctly more rounded than shard-like.

Oxidation of 5-aminotetrazole to 5-nitrotetrazole was shown to occur in high yields in the polar aprotic solvent DMSO in the presence of molecular sieves. Sodium 5-nitrotetrazolate was isolated from the reaction mixture in aqueous solution in yields that are competitive to current nitrotetrazole syntheses, but with the advantage that all energetic material handling occurs in solution. This method of sodium nitrotetrazolate synthesis offers a considerable safety increase over current methods as no intermediate primary explosives are dealt with (e.g. $Cu(NT)_2 \cdot HNT$) and the unstable diazotetrazole is entirely avoided. Furthermore, this method of sodium nitrotetrazolate production results in a material pure enough for use in DBX-1 synthesis without additional purification.

Experimental Section

CAUTION! The described compound 2 is energetic material with sensitivity to various stimuli. Potassium superoxide is a strong oxidizer that reacts with water in a very exothermic reaction releasing oxygen gas. While we encountered no issues in the handling of these materials, proper protective measures (face shield, lab coat, ear protection, body armor, and Kevlar gloves) should be used at all times and at larger scales the reaction should be conducted behind shielding. Caution should be observed should one attempt this chemistry with other solvents as in the case of sulfolane one attempt led to a rapid exotherm and ejection of reaction mixture.

General

All reagents, solvents and ion exchange resins were used as received (Sigma-Aldrich, Fluka, Acros Organics, Fisher Scientific Co LLC) if not stated otherwise. 3 Å molecular sieves were dried in an 300° C. oven under vacuum for 4 hours prior to use. Mass spectra and quantitative sampling was performed with an Agilent 1260 Infinity II Qua-ternary LC instrument. Crystal imaging was done with a Hirox RH-8000 digital microscope with a MXB-10C zoom lens and a OL-35011 adapter for 350-3500× magnification.

Reaction Yield Quantification

Each reaction yield was quantified using an Agilent 6200 infinite series LC-MS. A calibration curve was created by carefully measuring out known amounts of NaNT and buffer (1M $NH_4HCO_3$) into aqueous solution. The solution was diluted in volumetric flasks to 12 different concentrations to be run through the HPLC, outputting a corresponding peak integration area. The area was linearly correlated to the nitrotetrazolate content, and possessed a coefficient of determination of 95%, giving a 5% inherent error in quantification.

To quantify a reaction yield, a representative sample (between 0.250 g and 0.4 g) of the stirred reaction solution was weighed in a tared 25 mL volumetric flask containing ice water and approximately 2 mL of buffer, 1M $NH_4HCO_3$. The flask was then diluted to 25 mL with distilled water, and a portion of the quenched solution was transferred to an HPLC vial. Following analysis, if concentrations were found to be above the range of the calibration curve, the solution was diluted by transferring 1 mL of quenched solution to a 10 mL volumetric flask, filling to the line with water, and re-analyzing in HPLC.

Synthesis of Sodium Nitrotetrazolate

To the reaction vessel was added 82.5 mL (75 g) of anhydrous dimethyl sulfoxide (DMSO) and 10.0 g of dried 3 Å molecular sieves and/or 18-crown-6 (0.5 g, 1.9 mmol)] The contents were briefly stirred and 1.0 g (11.7 mmol) of 5-aminotetrazole were added. Potassium superoxide (4.5 g, 62.7 mmol, 5.3 eq.) was added to the vessel, which was vented with a drying column containing calcium chloride. The reaction was stirred continuously at room temperature and was sampled according to the procedure given in the Reaction Yield Quantification section. The reaction proceeded until nitrotetrazole yield plateaued (in-situ yields of 83-85% via quantitative HPLC), after which it was subjected to the final workup.

Once maximum yield is reached, reaction was quenched in approximately 250 mL of ice water buffered with ammonium bicarbonate. The solution was filtered and washed with distilled water. 1 eq. of tri-n-butylammonium sodium sulfate was added to the filtrate as a 1M solution and swirled. The cloudy solution was then lightly acidified to a pH of 6 and extracted (9×75 mL) into ethyl acetate. The organic layers were combined and the solvent evaporated to yield a thin oil. The product was re-dissolved in water and stirred over sodium-loaded ion exchange resin to give the desired product, sodium nitrotetrazolate in water. The final NaNT solutions after filtration of molecular sieves were quantified again by HPLC. Isolated yields by quantitative HPLC 48-53%.

Those skilled in the art will recognize that numerous modifications can be made to the specific implementations described above. The implementations should not be limited to the particular limitations described. Other implementations may be possible.

We claim:

1. A method of preparing a compound of Formula I:

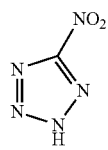

or any salt thereof,
wherein the method comprises:
providing a solvent system comprising a polar aprotic organic solvent and/or water;
providing 5-amino-1H-tetrazole or any salt thereof;
providing a superoxide anion source ($O_2^-$);
providing a crown ether and/or a molecular sieves;
adding said 5-amino-1H-tetrazole or any salt thereof, said superoxide anion source, said crown ether and/or molecular sieves to said solvent system; and
allowing said 5-amino-1H-tetrazole or any salt thereof to be oxidized to the compound of Formula I or any salt thereof.

2. The method of claim 1, wherein said superoxide anion source ($O_2^-$) comprises a superoxide salt of a metal, wherein the metal is an alkali metal, an alkaline earth metal, or a transition metal.

3. The method of claim 1, wherein said superoxide anion source comprises superoxide salt of Potassium, Titanium, Tungsten, Vanadium, Zirconium, or Tungsten.

4. The method of claim 1, wherein said crown ether is 18-crown-6.

5. The method of claim 1, wherein said polar aprotic organic solvent is dimethyl sulfoxide (DMSO), dimethylformamide (DMF), acetonitrile (MeCN), sulfolane, or N-Methyl-2-pyrrolidone (NMP).

6. The method of claim 1, wherein said 5-amino-1H-tetrazole or any salt thereof is oxidized at room temperature.

7. The method of claim 1, wherein the compound of Formula I or any salt thereof is prepared under a substantially anhydrous condition prior to any workup step.

8. The method of claim 1, wherein an organic ammonium salt of said compound of Formula I is prepared during one or more workup steps as an intermediate salt of the compound of Formula I, the intermediate salt of the compound of Formula I can be transferred from an aqueous solution to an organic solution by extraction.

9. The method of claim 8, wherein the compound of Formula I is obtained as an alkali metal salt after one or more workup steps.

10. The method of claim 9, wherein the compound of Formula I is obtained as a sodium salt after one or more workup steps.

11. The method of claim 10, wherein the sodium salt of the compound of Formula I is obtained from said organic ammonium salt of said compound of Formula I, by first dissolving said organic ammonium salt in water and then contacting the formed dissolved solution with a sodium-loaded ion exchange resin to give provide an aqueous solution of the sodium salt of the compound of Formula I.

12. The method of claim 8, wherein the organic ammonium salt is a tributylammonium salt.

* * * * *